United States Patent
Motamedi et al.

(10) Patent No.: US 10,089,074 B2
(45) Date of Patent: Oct. 2, 2018

(54) RELATIONSHIP ANALYSIS UTILIZING BIOFEEDBACK INFORMATION

(71) Applicant: ONTOLEAD, INC., La Jolla, CA (US)

(72) Inventors: Firoozeh Motamedi, La Jolla, CA (US); Shahrokh Yadegari, La Jolla, CA (US)

(73) Assignee: ONTOLEAD, INC., La Jolla, CA (US)

( * ) Notice: Subject to any disclaimer, the term of this patent is extended or adjusted under 35 U.S.C. 154(b) by 0 days.

(21) Appl. No.: 15/644,601

(22) Filed: Jul. 7, 2017

(65) Prior Publication Data

US 2018/0011689 A1    Jan. 11, 2018

Related U.S. Application Data

(60) Provisional application No. 62/360,186, filed on Jul. 8, 2016.

(51) Int. Cl.
| | |
|---|---|
| *G01N 33/48* | (2006.01) |
| *G01N 33/50* | (2006.01) |
| *G06F 7/02* | (2006.01) |
| *A61B 5/053* | (2006.01) |
| *A61B 5/16* | (2006.01) |

(52) U.S. Cl.
CPC .............. *G06F 7/02* (2013.01); *A61B 5/0533* (2013.01); *A61B 5/167* (2013.01)

(58) Field of Classification Search
None
See application file for complete search history.

(56) References Cited

U.S. PATENT DOCUMENTS

| | | | |
|---|---|---|---|
| 6,605,038 B1 | 8/2003 | Teller | |
| 2008/0270438 A1 | 10/2008 | Aronson et al. | |
| 2009/0298054 A1* | 12/2009 | Lesche | C12Q 1/6886 435/6.12 |
| 2013/0296987 A1* | 11/2013 | Rogers | A61F 7/007 607/112 |

FOREIGN PATENT DOCUMENTS

| | | |
|---|---|---|
| JP | 2001195504 A | 7/2001 |
| KR | 20070122012 A | 12/2007 |
| WO | 2013/044185 A2 | 3/2013 |

OTHER PUBLICATIONS

Lim et al. International Journal of Psychophysiology, vol. 25, 1997, pp. 97-109.*
Lim et al.,"Decomposing skin conductance into tonic and phasic components," Int J Psychophysiol; Feb. 25, 1997; (2):97-109.
Benedek et al., "A continuous measure of phasic electrodermal activity," J Neurosci Methods; Jun. 30, 2010; 190 (1-5):80-91.

* cited by examiner

*Primary Examiner* — Russell S Negin
(74) *Attorney, Agent, or Firm* — Pillsbury Winthrop Shaw Pittman LLP

(57) ABSTRACT

First sensor data may be acquired from a first galvanic skin response sensor monitoring a first user. Second sensor data may be acquired from a second galvanic skin response sensor monitoring a second user. At least one programmable processor may generate a compatibility score between the first user and the second user. The generating may include executing a compatibility algorithm to generate the compatibility score based at least on a comparison of at least one type of response contained in the first sensor data and the second sensor data. A client device may generate an electronic indication of the compatibility score.

19 Claims, 11 Drawing Sheets

RELATIONSHIP ANALYSIS UTILIZING BIOFEEDBACK INFORMATION

CROSS-REFERENCE TO RELATED APPLICATIONS

The current application claims priority under 35 U.S.C. § 119 to U.S. Provisional Patent Application No. 62/360,186 filed Jul. 8, 2016 and entitled "RELATIONSHIP ANALYSIS UTILIZING BIOFEEDBACK INFORMATION," the contents of which are hereby incorporated by reference in their entirety.

BACKGROUND

Relationship decisions are made on many different levels and in many different situations. For example, when seeking out a romantic mate, people can decide based on gut feelings, attraction, or background checks. Relationship decisions also occur in the formation of groups, for example, for social or work-related purposes. The personalities of the individuals in the group, and how they relate to one another, will affect the operation of the group and the potential of the group to meet its goals.

SUMMARY

In a first aspect, a computer program product is disclosed. The computer program product may include a non-transient, machine-readable medium storing instructions which, when executed by at least one programmable processor, cause the at least one programmable processor to perform operations. These operations may include receiving, at the at least one programmable processor, first sensor data acquired from a first galvanic skin response sensor monitoring a first user. The operations may also include receiving, at the at least one programmable processor, second sensor data acquired from a second galvanic skin response sensor monitoring a second user. The at least one programmable processor may generate a compatibility score between the first user and the second user. The generating may include executing a compatibility algorithm to generate the compatibility score based at least on a comparison of at least one type of response contained in the first sensor data and the second sensor data. A client device may generate an electronic indication of the compatibility score.

In some variations, the at least one type of response may include a tonic response and a phasic response. The first sensor data may include first phasic data and first tonic data, and the second sensor data may include second phasic data and second tonic data. The phasic data may correspond to the phasic response and the tonic data may correspond to the tonic response. Also, the operations may further include separating, by at least a first discrete decomposition analysis, the first sensor data into a first tonic response and a first phasic response. Also the operations may further include separating, by at least a second discrete decomposition analysis, the second sensor data into a second tonic response and a second phasic response.

In other variations, first tonic data and second tonic data may be extracted from the first sensor data and the second sensor data. The comparison may be further based on the first tonic data and the second tonic data.

In yet other variations, first phasic data and second phasic data may be extracted from the first sensor data and the second sensor data. The comparison may be further based on the first phasic data and the second phasic data.

In some variations, the compatibility score may be generated by at least performing statistical analysis of first tonic data and second tonic data extracted from the first sensor data and the second sensor data. The compatibility score may also be generated by at least performing statistical analysis of first phasic data and second phasic data extracted from the first sensor data and the second sensor data.

In other variations, a first statistical analysis of first tonic data and second tonic data extracted from the first sensor data and the second sensor data may be performed. Also, a second statistical analysis of first phasic data and second phasic data extracted from the first sensor data and the second sensor data may be performed. The compatibility score may be based at least on the first statistical analysis and the second statistical analysis.

In some variations, generating of the compatibility score may further include performing a first linear regression analysis of the tonic data of the first user and the second user. A first ratio of a tonic variance between the first user and the second user may be calculated. A second linear regression analysis of the phasic data of the first user and the second user may be performed. A second ratio of a phasic variance between the first user and the second user may be calculated.

In other variations, the compatibility score may be proportional to an average of the first ratio and the second ratio, and the compatibility score may be proportional to a measure of agreement in the first linear regression analysis or the second linear regression analysis for the first user and the second user.

In some variations, at least one of the first sensor data or the second sensor data may include an event window containing a number of peaks in the first sensor data or the second sensor data.

In yet other variations, the number of peaks in the first sensor data or the second sensor data may be clustered to generate an event value for a portion of the first sensor data or the second sensor data. The clustering may include filtering the first sensor data or the second sensor data to identify the number of peaks in the first sensor data or the second sensor data present in the event window that have an amplitude of at least a threshold value. The event value may be generated based on the number of the peaks in the event window. The first ratio, the second ratio, or the linear regression analysis may be based at least on the event value.

In other variations, an input device may receive an evaluation characterizing the first sensor data or the second sensor data in an event window. The compatibility score may be based in part on the evaluation.

In some variations, user input may be received from the first user specifying a desired feature of the second user. The compatibility algorithm may increase the compatibility score when the second sensor data reflects the desired feature. Also, a first user at a graphical interface of an input device may select the desired feature of the second user from a predefined list that includes a calmness or an excitability. The compatibility algorithm may generate the compatibility score based at least on an objective determination that the second user has the desired feature through analysis of the second sensor data. The calmness or the excitability may be determined based at least on statistical analysis of the tonic data or the phasic data of the second user.

In other variations, permission settings entered at an input device by the first user may be received. Access by the second user to at least one of first sensor data or analyzed first sensor data generated by the compatibility algorithm when generating the compatibility score may be restricted based at least on the permission settings.

In other variations, the sensor data may be filtered, by at least applying principle component analysis, to exclude one or more types of the sensor data. The filtering may remove at least one component of the sensor data as identified by the principle component analysis.

In an interrelated aspect, a system is disclosed. The system may include a first galvanic skin response sensor configured to monitor a first user, a second galvanic skin response sensor configured to monitor a second user, at least one programmable processor, and a non-transient machine-readable medium storing instructions which, when executed by the at least one programmable processor, cause the at least one programmable processor to perform operations. The operations may include receiving, at the at least one programmable processor, first sensor data acquired from the first galvanic skin response sensor monitoring the first user. The operations may also include receiving, at the at least one programmable processor, second sensor data acquired from the second galvanic skin response sensor monitoring the second user. The at least one programmable processor may generate a compatibility score between the first user and the second user. The generating may include executing a compatibility algorithm to generate the compatibility score based at least on a comparison of at least one type of response contained in the first sensor data and the second sensor data. A client device may generate an electronic indication of the compatibility score.

In some variations, the system may include a complementary device configured to receive user input and add an evaluation to the first sensor data or the second sensor data. The evaluation may provide a numerical weight to the first sensor data or the second sensor data when generating the compatibility score.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
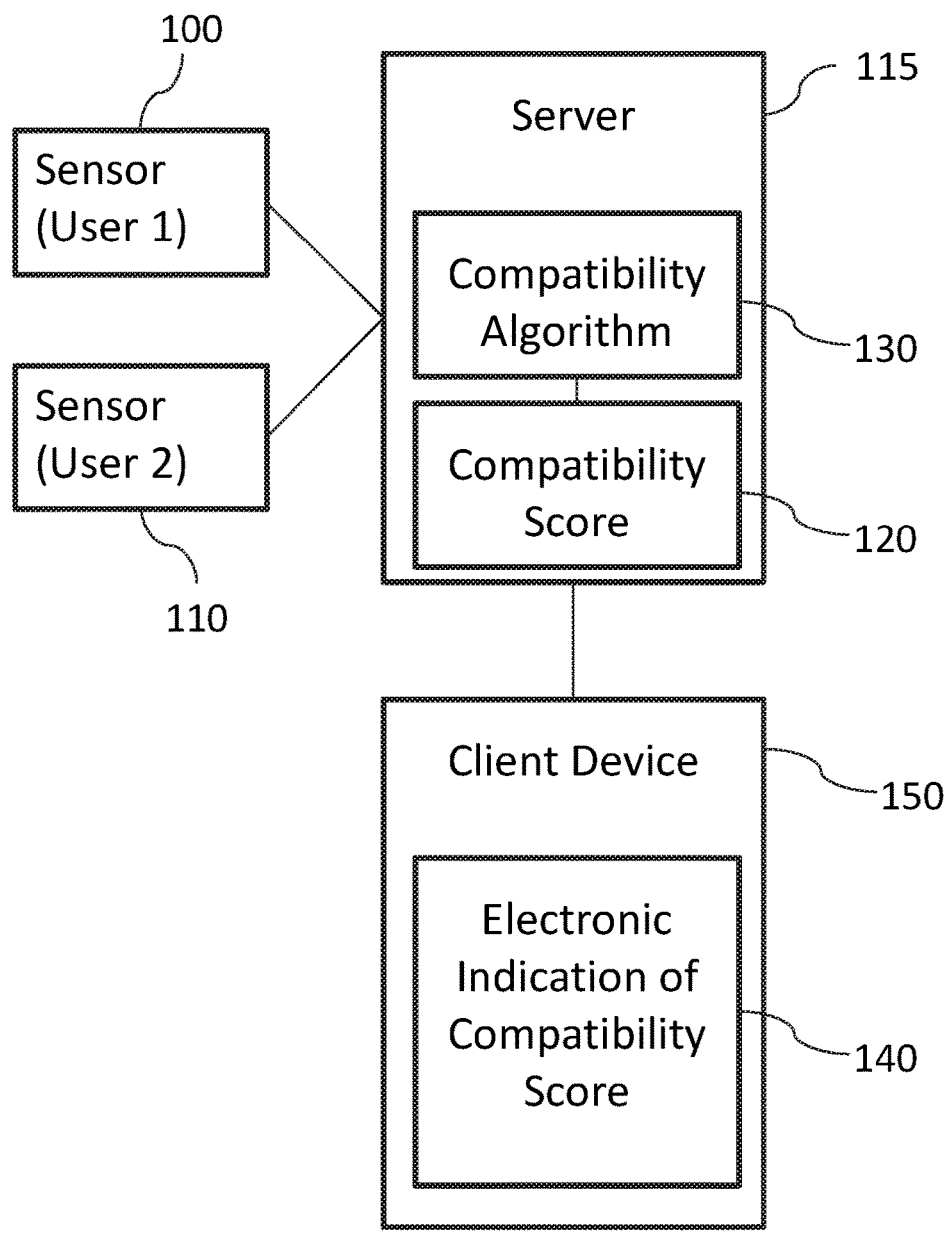
FIG. 1 is a diagram illustrating a simplified system for generating and presenting a compatibility score based on sensor data in accordance with certain aspects of the present disclosure.

FIG. 1 illustrates a simplified system for generating and presenting a compatibility score 120 based on sensor data in accordance with certain aspects of the present disclosure. The present disclosure describes systems, methods, and computer software for gathering, storing, and analyzing sensor data from two or more individuals in, for example, the context of monitoring and maintaining relationships between them. As shown in FIG. 1, this can include executing a compatibility algorithm 130 at a server (or other computing device) with the sensor data being input into the compatibility algorithm 130.

The compatibility algorithm 130 can generate a compatibility score 120 based on the analyzed sensor data. The compatibility score 120 can be a metric indicative of the compatibility or harmony between the two or more individuals based on, for example, their respective sensor data and their compatibility preferences. The compatibility score 120 can be provided, for example, in the form of electronic data or as an electronic indication 140 (e.g., graphical, audio, textual, etc.) generated at a client device 150 (e.g., a smart phone, tablet computer, personal computer, etc.). Some non-limiting examples of uses and implementations of the system are provided below.

Match Evaluator—Users of the system can wear sensors whose sensor data can be continuously analyzed and uploaded to the cloud or other remote computing system through a wired or wireless network connection. Users can define their preferences for the type of people they are interested in. These preferences can include, for example, an indication of a lifestyle that can be extracted from sensor data (e.g., how active a person is, how excited do they get, what form of excitement 'tonic/phasic' they have). By matching the user's preferences to the sensor data of other users, the system can provide match suggestions to the user based on a compatibility score 120. Compatibility scores can be presented as, for example, a value between 0 and 1, which can be translated to, for example, "Great Fit", "Good Fit", "Not Bad", "Little Fit", or "No Fit".

Personal Date Evaluator—Another example can include a user who has been wearing the sensors, and the sensor data has previously been uploaded to the system. The user can go on a date while wearing the sensor(s) or sensing device. The system can analyze and report the quality of the date based on the gathered sensor data, the user's lifestyle, and the user's preference for the type of reaction the user has selected as the best reactions to have on a date (this selection can define the level of excitement, the frequency of excitation, and the shape of features in the sensor data that correspond to various causes of excitement). The user can then input his or her evaluation of the date which can be used to train the system to learn about the user's preferences.

Date Match Evaluator for Two—In another implementation, two users who have been wearing sensors (and whose sensor data has been uploaded to the system), can go on a date while both are wearing the sensors and both have given each other access to their sensor data for the purpose of evaluation. The system can determine that the date has occurred based on GPS information obtained from the two sensors. The system can analyze and report the correlation of the recorded sensor data and compatibility of the two users with each other. If the users continue to have future dates, the system can analyze each of the dates, as well as record and monitor the evolution of the dates between the two users. The system can also report the quality of each date based on the ongoing evolution of the compatibility score 120 associated with each date.

Speed-Date Match Evaluator—A user wearing the sensor can go to a speed dating event (e.g., where many individuals come to meet each other and each couple will have specific amount of time to talk to each other, for example, around 5 to 10 minutes). The system can report about the quality of pairings individually to each user, or the system can cross analyze the compatibility score 120 generated from the sensor data between the participants who also have worn the sensors and are participants of the system described herein.

Relationship Harmony Measure—In another implementation, two users who have been wearing the sensing devices, and whose data have been uploaded regularly, can monitor their sensor data analysis and compare with their relationship partner. The sensors or other devices can also track their proximity to each other. The system can analyze and report on the correlation of their sensor data and their compatibility in their everyday life (e.g., when they are apart) in comparison to the times when they are close to each other. This can provide a measure of feedback on how their personal compatibility compares with their compatibility with people in general. The system can also provide feedback on the synchronization of their sensor data during their respective sleep cycles.

As used herein, sensor data, also sometimes referred to herein as "biofeedback data," or "biofeedback" can include, but is not limited to, any type of measurable data relating to a physical, mental, or physiological state. The sensor data can include, for example, temperature, heart rate, electrodermal activity (e.g., skin conductance), data relating to blood, urine, sweat, hormone, pheromone, saliva, catecholamine levels, metanephrine levels, measurements of minerals in sweat, and DNA. Other types of sensors can provide motion/acceleration measurements, muscle activity, brain activity (e.g., magnetoencephalography), other organ activity (e.g., EEG, EKG), body imaging (MRI, X-Ray), audio recording, visual images, video recording, positional information (e.g., GPS coordinates), and the like.

Figure 2:
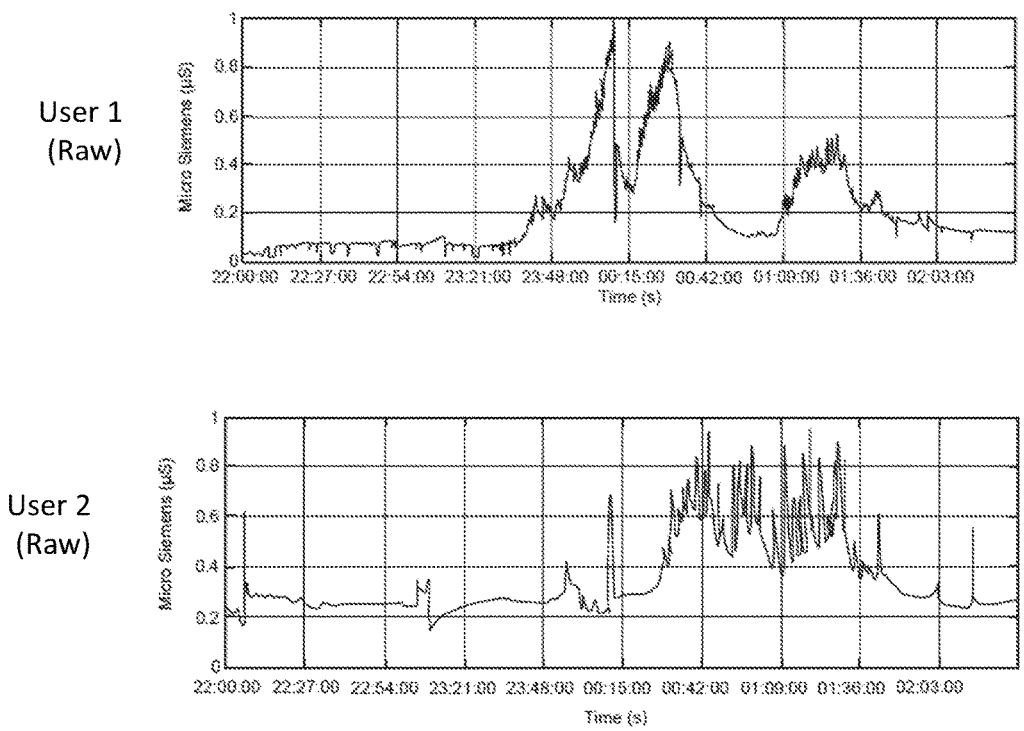
FIG. 2 is a diagram illustrating an example of sensor data acquired from two users in accordance with certain aspects of the present disclosure.

FIG. 2 illustrates an example of sensor data acquired from two users in accordance with certain aspects of the present disclosure. Sensor data can include, for example, analog or digital data received from the sensors or the sensing device. FIG. 2 shows an example time-resolved plot of sensor data acquired from sensors connected to a first user and a second user. In this example, the first sensor data and the second sensor data can be based on at least electro-dermal activity of the first user and the second user measured by the first sensor 100 and the second sensor 110. The gathering of the sensor data can be through one or more sensors operatively coupled to a sensing device or through other electronic devices. The sensing device can gather sensor data continuously, or on demand, from the subject.

In some implementations, a sensing device that contains one or more sensors can be, for example, a watch, wristband, electrode, or other external device that monitors or records sensor data for a user. The types of sensors that can be incorporated into the sensing device can include, for example, a photoplethysmography sensor, for measuring Blood Volume Pulse (BVP) and Heart Rate Variability (HRV), an accelerometer, an EDA sensor (or galvanic skin response GSR) sensor, and an infrared Thermopile sensor (for skin temperature). Other kinds of sensors can include electrochemical biosensors, optical biosensors, electronic biosensors, piezoelectric biosensors, gravimetric biosensors, or pyroelectric biosensors, and the like.

The sensor can be, for example, close to the body (either in direct contact or not), attached to the body, planted under the skin, inserted in the body (implants or nano-sensors), or inserted in the blood stream (nano-sensors). The sensing device can have its own internet connectivity capability and can send sensor data to a recipient device or computer as the sensor data is being acquired. The sensing device can also be connected to a network through a wire connection or wirelessly, for example with Bluetooth technology, to a local device. The local device can act as an intermediary or relay for transfer of sensor data to the server 115. Local devices can include, for example, a mobile phone or a tablet, with internet capabilities. The sensor data can be transferred to the cloud or other connected computing system in real-time when the sensor data is being gathered. The sensing device can also have its own computer memory and, when connection with the internet is established, it can send the gathered sensor data at a different time than the time that the sensor data is being gathered. In such implementations, the sensor data can be accumulated until a connection is established that allows the transfer of the sensor data to the desired computing system, for example, the server 115 illustrated in FIG. 1. The sensing device, the local mobile device, and or the server 115, can keep the sensor data in a raw format or analyze the sensor data as explained in greater detail below.

In some implementations, the sensing device or a complementary device can also record user-specified markers (e.g., identifying or time stamping events associated with the received sensor data).

Specific examples of complementary devices that can add information to the sensor data can include a clicker (e.g., a button or trigger) that can be on the sensor or another device (such as a cellphone). Single, double, and triple clicks can have different meanings, for example, a single click can mark an event selected by a user from a pre-selected list, a quick double click can be recorded as a positive event, and a quick triple click can be recorded as a negative event. A rotary button can allow the user to pick from a set of pre-selected evaluations such as: a very pleasant event—evaluation: 0.9, pleasant event—evaluation 0.7, average event—evaluation 0.5, negative event—evaluation 0.3, or a very negative event—evaluation 0.1. These evaluations can be implemented to provide weights to specific portions or features of the sensor data, as described further herein.

In other implementations, a clicker and rotary button can be used in conjunction with each other, a microphone can be used for the user to use voice to assign an evaluation to an event, or a video camera can be used for the user to use voice to assigning an evaluation to an event.

Figure 3:
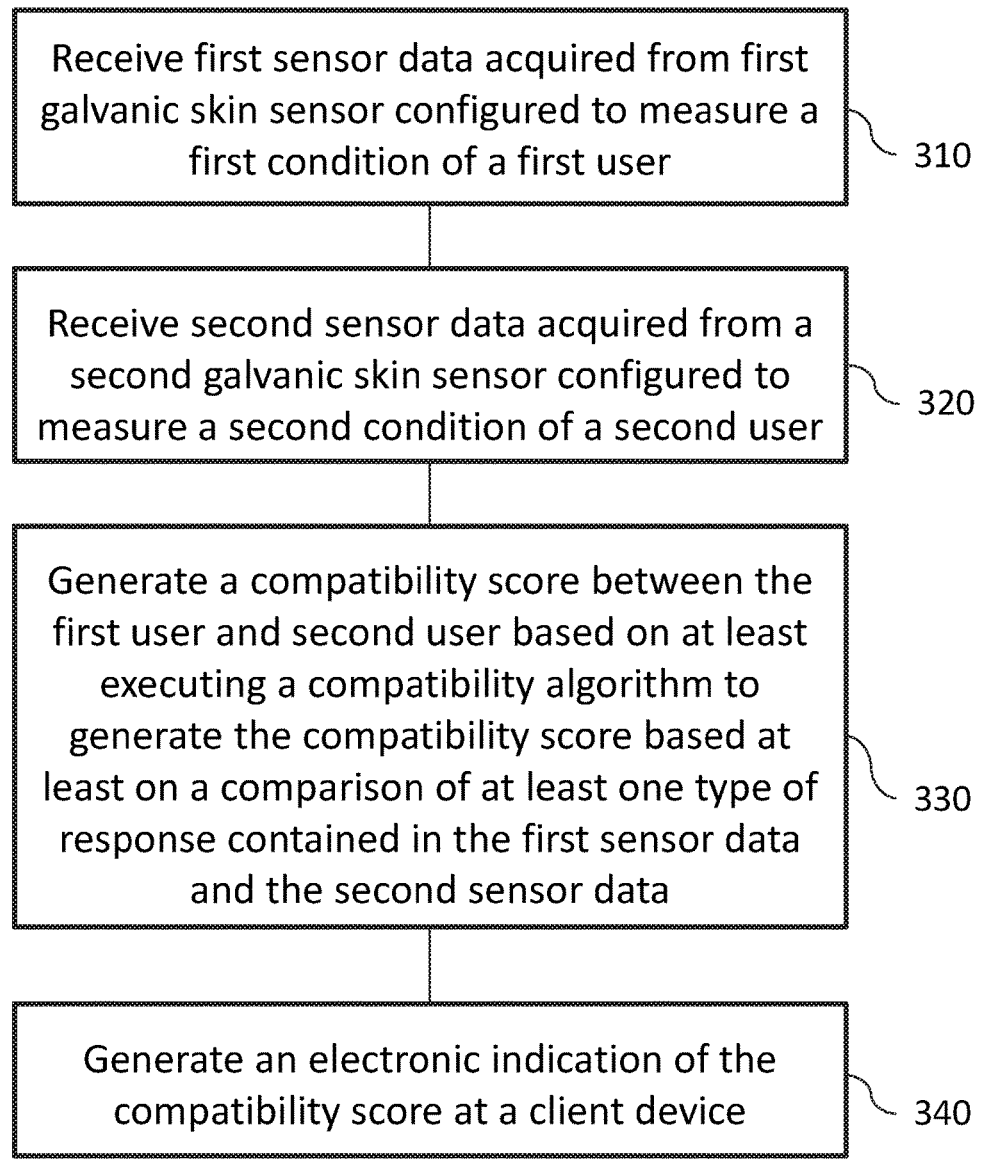
FIG. 3 is a process flow diagram illustrating generating a compatibility score based on sensor data in accordance with certain aspects of the present disclosure.

FIG. 3 is a process flow diagram illustrating generating a compatibility score 120 based on sensor data in accordance with certain aspects of the present disclosure. In one implementation, the systems, computer program products, and methods described herein can include, at 310 receiving first sensor data acquired from a first sensor 100 monitoring a first user. In some implementations, the monitoring of the user can be performed in real-time and generally simultaneous with the ongoing analysis of the sensor data. In other implementations, the monitoring can have been performed previously with the sensor data stored and/or transmitted to a server or other computing device that can analyze the data as described herein.

At 320, second sensor data can be received that was acquired from a second sensor 110 monitoring a second user.

At 330, a compatibility score 120 between the first user and the second user can be generated. The generating can include executing a compatibility algorithm 130 to generate the compatibility score 120 based at least on a comparison of at least one type of response contained in the first sensor data and the second sensor data.

At 340, a client device 150 can generate an electronic indication 140 of the compatibility score 120.

A sensor, as used herein, refers to the particular sensor that enables the sensing device to function in its prescribed manner. For example, when the sensing device is an electrodermal device or galvanic skin response sensor configured to measure skin conductance (which can change in response to an increase or decrease in a person's sweating), the sensor can be two electrical contacts having a potential difference. The amount of current transferred between the two electrical contacts comprising sensor can be related to the change in the skin conductance. As another example, a thermometer can be a sensing device that includes a thermocouple as a sensor.

A sensing device, as used herein, refers to a device that is directly connected to or operatively coupled with one or more sensors. The sensing device can include, for example, any combination of receivers, transmitters, and transceivers that can be configured to transmit or receive data to or from the sensing device. Examples of sensing devices can include, for example, a smartwatch with sensing capabilities, a medical device configured to acquire physical data about a person, a camera that can view a person or a portion of a person's anatomy, a microphone that can be used to generate audio recordings of a person, or the like.

As used herein, a "response" or "type of response" contained in the sensor data refers to a discrete and quantifiable aspect of the sensor data that can be identified in the raw sensor data or extracted or derived from the raw sensor data or processed sensor data through data analysis. Examples or responses or types of responses that can be present in sensor data can include, but are not limited to, a tonic response, a phasic response, a high-frequency response, a low-frequency response, a change in the amplitude or shape of the sensor data, or the like. Certain types of responses can be extracted from processing the sensor data, for example by applying low-pass filtering to extract a low-frequency response.

Terms such as "objective analysis," "objective data," or the like, as used herein, generally refer to analysis and data based purely on actual data acquired from a sensor or the analysis of same. In contrast, terms such as "subjective analysis," "subjective data," or the like, as used herein, generally refer to analysis and data that has some component that has been defined by the user. In this section, features relating to "objective analysis" are discussed. Later, features relating to "subjective analysis" are discussed.

Figure 4:
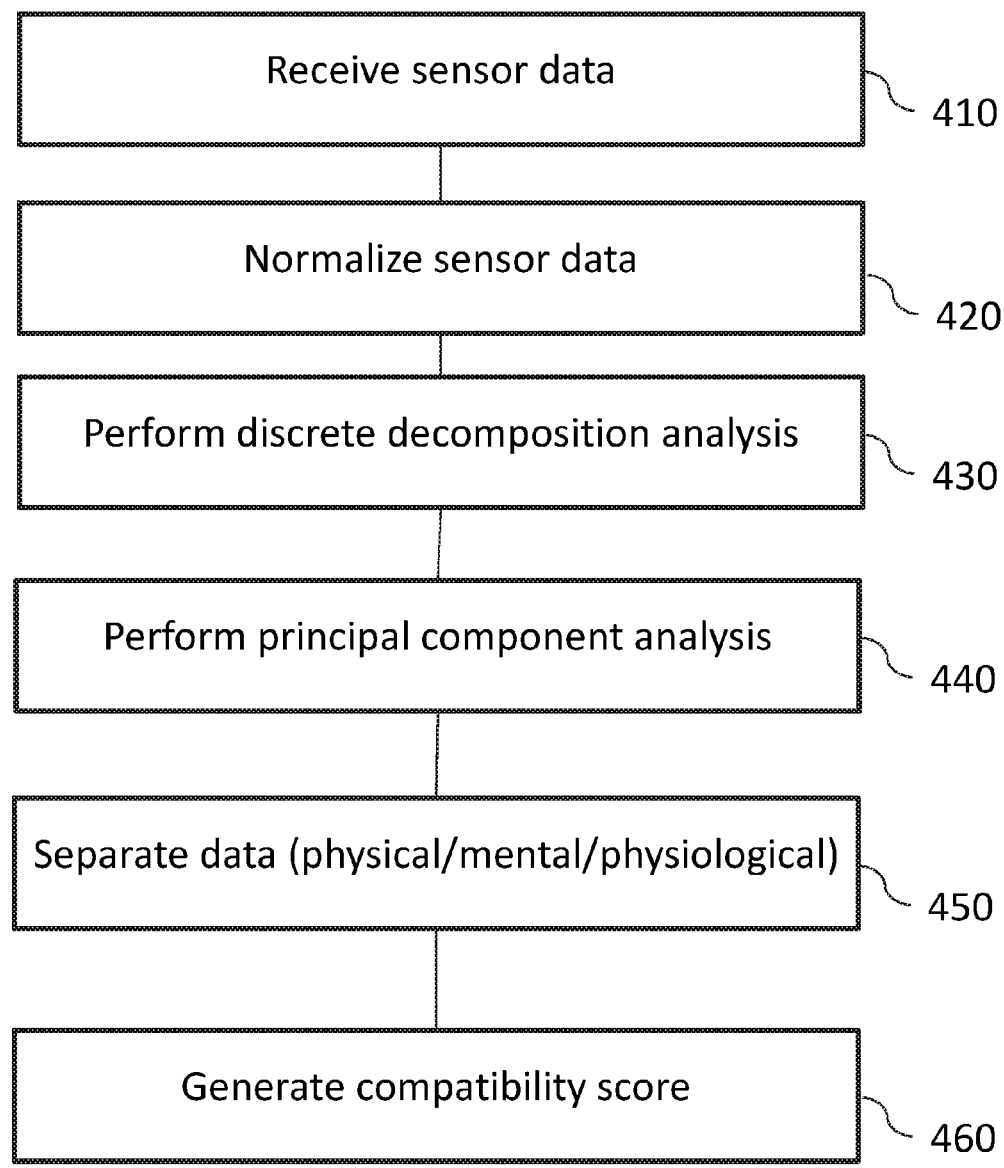
FIG. 4 is a process flow diagram illustrating an example of certain manipulation and analysis of sensor data in accordance with other aspects of the present disclosure.

FIG. 4 is a process flow diagram illustrating an example of certain manipulation and analysis of sensor data in accordance with other aspects of the present disclosure. Analysis of the sensor data can be performed by the compatibility algorithm 130 to generate a compatibility score 120 relating to the users providing the sensor data. The analysis described below can include, for example, at 410, receiving the sensor data, at 420, normalizing the sensor data, at 430, performing discrete decomposition analysis to identify the types of responses present in the sensor data, at 440, performing principal component analysis to exclude some sensor data that is not as relevant as other types of sensor data, at 450, separating the sensor data into categories such as physical data, mental data, or physiological data, and, at 460, generating the compatibility score.

In some implementations, the sensor data can be normalized to a specified range (e.g., 0-1, 1-10, 1-100, −1 to +1), etc.). Such a normalization can be used to account for differences in diagnostic sensitivity, the individual response of a person to an event, the particular differences in a person's response in terms of a particular type of sensor data, or the like. For example, the sensor data from a first user and a second user can be normalized to both be in a range of 0-1 in order to facilitate later analysis. Such normalization can be applied at any stage of the analysis.

Figure 5:
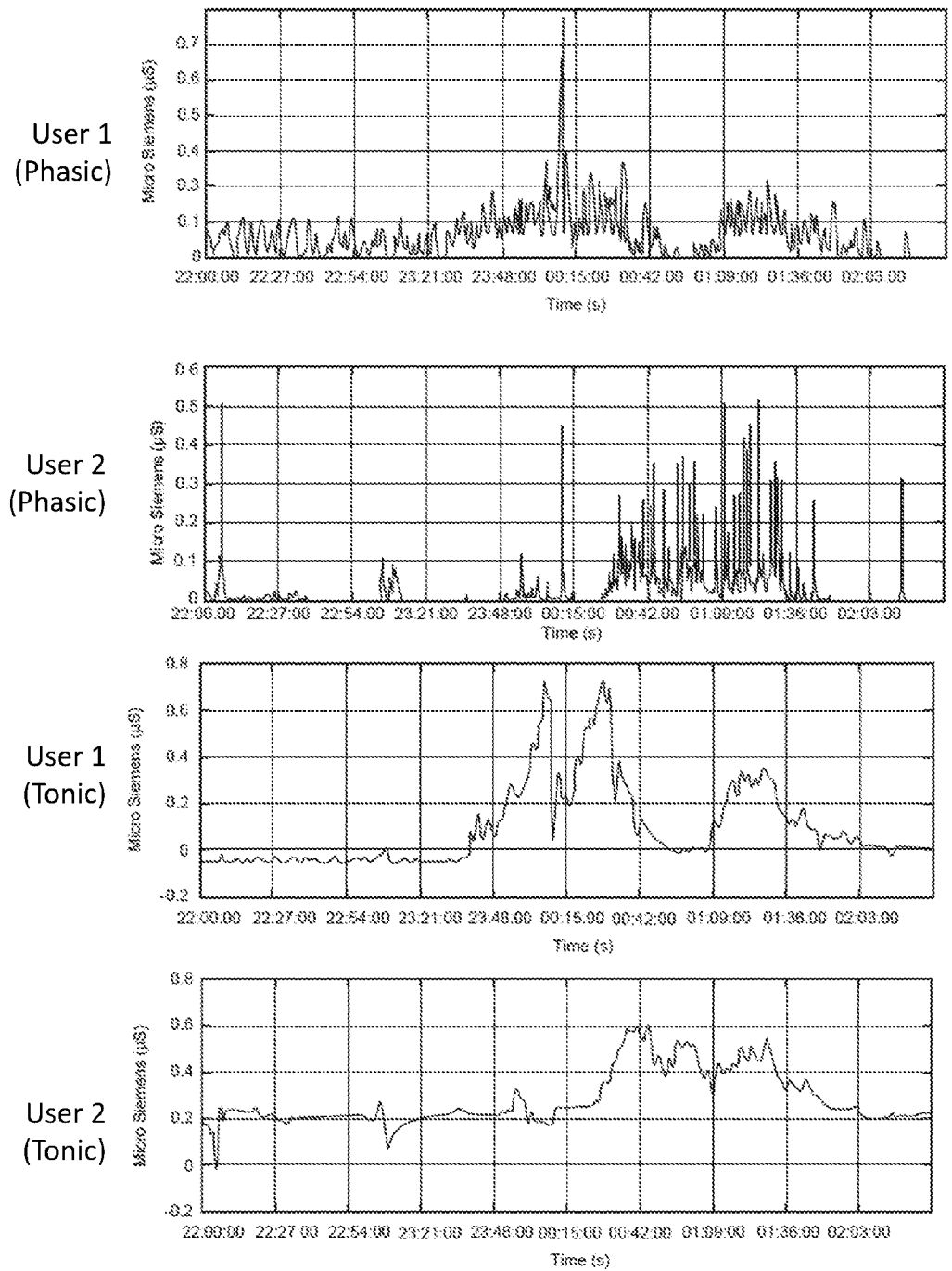
FIG. 5 is a diagram illustrating an example of phasic data and tonic data generated through discrete decomposition analysis in accordance with certain aspects of the present disclosure.

FIG. 5 is a diagram illustrating an example of phasic data and tonic data generated through discrete decomposition analysis in accordance with certain aspects of the present disclosure. The sensor data can also be separated into or otherwise identified as representing at least one type of response (e.g., a fast response and a slow response). A fast response (which can include a phasic response), can be sensor data that reflects a fast physiological response to an event or stimulus. In the specific case of a phasic response, the response captured in the sensor data is generally not present or quickly diminishes once the stimulus is removed. For slow (or tonic) responses, the sensor data can include a response with a slow onset and/or decay time after the event and or after the stimulus has been removed. In some implementations, the sensor data can first be analyzed to extract the tonic data by smoothing the sensor data to provide a baseline. The baseline can then be subtracted from the sensor data to provide the phasic data. The degree of smoothing applied to the sensor data can be predefined in the system or can be set by a user. In other implementations, a negative deconvolution can be applied to the sensor data to separate the tonic data and the phasic data.

Accordingly, in some implementations, the at least one type of response can include a tonic response and a phasic response. The first sensor data can include first phasic data and first tonic data, and the second sensor data can include second phasic data and second tonic data. The phasic data can correspond to the phasic response and the tonic data can correspond to the tonic response. The operations performed in analyzing the sensor data can include separating, by at least a first discrete decomposition analysis, the first sensor data into a first tonic response and a first phasic response. Similarly, the operations can also include separating, by at least a second discrete decomposition analysis, the second sensor data into a second tonic response and a second phasic response.

Based on the presence of a tonic response and a phasic response, first tonic data and second tonic data can be extracted from the first sensor data and the second sensor data. Similarly, first phasic data and second phasic data can be extracted from the first sensor data and the second sensor data. The comparison of sensor data between the users can be further based on the first tonic data the second tonic data, the first phasic data and the second phasic data. As described herein, the comparison can be used to generate a compatibility score 120.

More particularly, some implementations can include performing statistical analysis on one or more of the tonic data, the phasic data, or any combination thereof to generate the compatibility score. Examples of statistical analysis such as linear regression and calculation of variance are described with reference to FIG. 7.

In some implementations, the tonic data can be considered. For example, the compatibility score can be generated by at least performing statistical analysis of first tonic data and second tonic data extracted from the first sensor data and the second sensor data.

In other implementations, the phasic data can be considered. For example, the compatibility score can be generated by at least performing statistical analysis of first phasic data and second phasic data extracted from the first sensor data and the second sensor data.

In yet other implementations, a combination of tonic and phasic data can be considered. For example, the compatibility algorithm 130 can perform a first statistical analysis of first tonic data and second tonic data extracted from the first sensor data and the second sensor data. Additionally, the compatibility algorithm 130 can also perform a second statistical analysis of first phasic data and second phasic data extracted from the first sensor data and the second sensor data. The compatibility score 120 can be based at least on the first statistical analysis and the second statistical analysis. Some specific implementations of these statistical analysis methods are described in further detail below.

To improve the correlation of the sensor data (which can include many types of measurements as discussed above) with a particular event, some types of sensor data can be removed or excluded from later analysis. Some implementations of the current subject matter can include filtering, by at least applying principle component analysis, the sensor data to exclude one or more types of the sensor data. The filtering can remove at least one component of the sensor data as identified by the principle component analysis. For example, if the sensor data included heart rate and GPS position, a given event such as a pain response may be more correlated with the user's heart rate than the GPS position provided by another sensor. The filtering can then remove the component (e.g., type of sensor data) that is not primarily correlated with the particular event that generated the sensor data.

The exclusion of sensor data can be performed by, for example, one or more of Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), and Flexible Discriminant Analysis (FDA).

In some implementations, the system can separate the sensor data into physical, physiological, and mental data. As used herein, "physical" data can be defined as all the changes in the sensor data that is generated through physical activity of the body. For example, some types of the sensor data of a person will increase while exercising (e.g., heart rate, sweating, and respiration). As used herein, "physiological" data is defined as all the data and fluctuations that are related to the bodily functions, but separate from intentional activity by a person. Examples of physiological data can include, how circadian clock affects our daily cycle, or how a women's monthly period can affect their sensor data, or how taking certain regular medication can affect the overall sensor data. "Mental" data is defined herein as the sensor data that can be generated through emotional and intellectual engagement of the user (often by the sympathetic nervous system) with events. Such data separation can be used to further filter or restrict the types of sensor data analyzed to determine the compatibility score 120.

In some implementations, after the discrete decomposition analysis is completed the sensor data can be analyzed with principal component analysis. All data that is highly correlated with sensors that measure physical activity (such as an accelerometer) can be classified as "physical data." Data can be aggregated over time to learn about physiological aspects of a user's body, and all the data that match this category will be classified as "physiological data." All the other data that is neither physical nor physiological can be classified as "mental data." These classifications of sensor data can be stored and, in some implementations, used at least in part as the basis for calculating the compatibility score 120.

Figure 6:
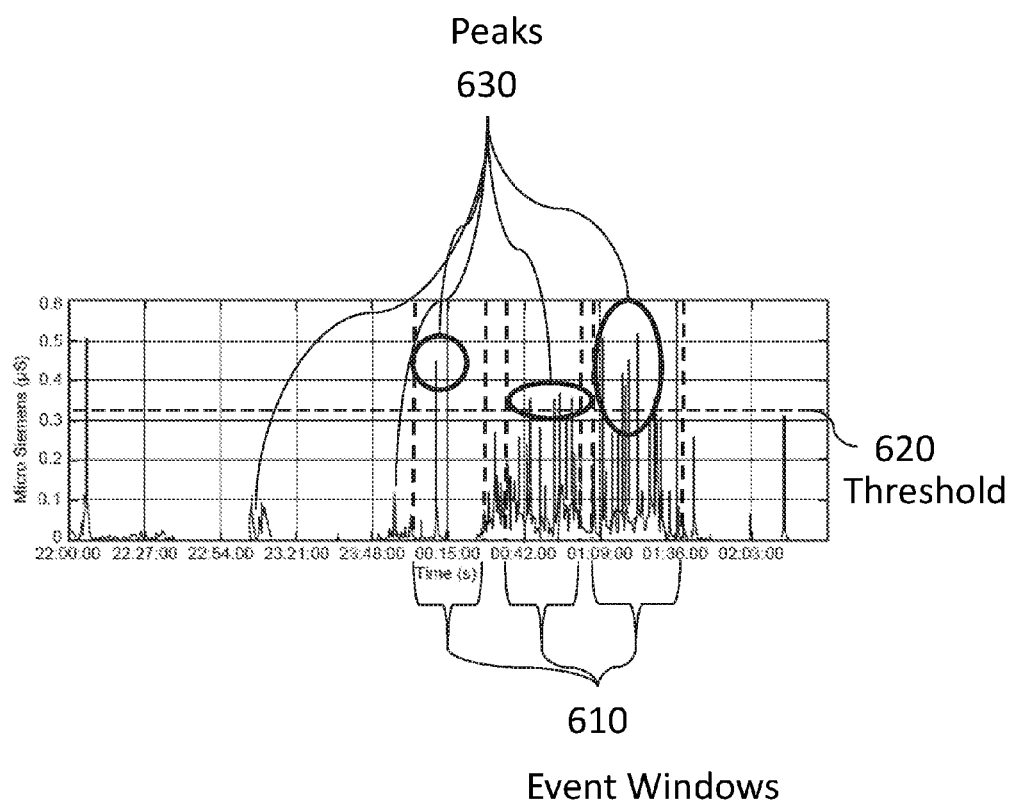
FIG. 6 is a diagram illustrating an example of the determination of an event value of exemplary phasic data in accordance with certain aspects of the present disclosure.

FIG. 6 is a diagram illustrating an example of the determination of an event value of exemplary phasic data in accordance with certain aspects of the present disclosure.

As used herein, an "event window" is any time window in the sensor data specified either by a user (such as providing a subjective evaluation of an event or interaction) or algorithmically (such as automatically by the systems herein or a separate system configured to identify event windows). The event window 610 can generally correspond to an event, for example a date, a greeting, a conversation, or the like. The sensor data can sometimes include a number of features during the event window 610 that can be further analyzed to quantify a specific type of reaction of a user to the event.

In some implementations, an attribute can be added to the sensor data in the event window 610. The attribute can include a name or other identifier of the event, time-stamps (e.g., noting that a particular feature of the sensor data occurred at a specific time or time window), or other similar metadata associated with the sensor data in the specified event window 610. Some attributes can be defined by the user through an input device and some attributes and event windows can be detected algorithmically by clustering features in the sensor data. Use of an input device is described further with reference to FIG. 11. The user can also define the event window 610 at the input device, or the system can automatically determine an appropriate event window 610.

As used herein, an "input device" 610 refers to any sort of mechanical or computing device that can receive input from a user and convert the input to a signal or data that can be interpreted by the compatibility algorithm. For example, an input device can be a smartphone, laptop computer, personal computer, complementary device, button, clicker, or the like.

Events that are represented by the sensor data can be rated, characterized, or generally quantified by analyzing features of the sensor data. These features can include the number of peaks above a particular threshold, the amplitude of the sensor data, particular features of the sensor data (e.g., shape of peaks, rise times, etc.), or the like. In some implementations, the event value (or intensity, amplitude, etc.) corresponding to an event window 610 (corresponding to a particular event) can be determined, by at least clustering a number of peaks in the sensor data to generate an event value for a portion of the sensor data. As used herein, "clustering" refers to identifying and grouping one or more features of the sensor data for further analysis, such as calculating an event value that corresponds to the clustered features of the sensor data. The event value can generally reflect the intensity of the event as it relates to a particular type of data. For example, an event can cause a strong response in the phasic data but not as strong in the tonic data. To determine the event value, the clustering can include filtering the sensor data to identify a number of peaks in the sensor data during the event window 610 that have an amplitude of at least a threshold value 620. The event value can be generated based on the number of peaks in the event window 610. These event values can serve as the basis for any of the statistical analysis applied to the sensor data. For example, as described further herein, the event value can be used to generate ratios of tonic or phasic data, or can be compared between two users with linear regression analysis.

Returning to the example of FIG. 6, the compatibility algorithm 130 (or the user) can define an event window 610 as spanning a particular time window, here shown by the dashed vertical lines in the plot and the brackets. During any of these event windows 610, a threshold value 620 for the phasic data can be applied. The number of peaks 630 that exceed the threshold value 620 can be counted and used to determine the event value. In this example, the first event window 610 contains a single peak 630 that exceeds the threshold 620. The latter two event windows 610 each contain several peaks 630 that exceed the threshold 620. In general, the more peaks 630 above threshold and the higher the amplitude of the peaks 630, the stronger the event is considered to be as it relates to the type of sensor data. In other implementations, the event value can be calculated relative to a baseline, and can be positive or negative, with the threshold value being below the baseline for "negative" peaks. In some implementations, the system can assign to the event value, or the sensor data in the event window 610, a timestamp that coincides with the midpoint of an event window 610.

Figure 7:
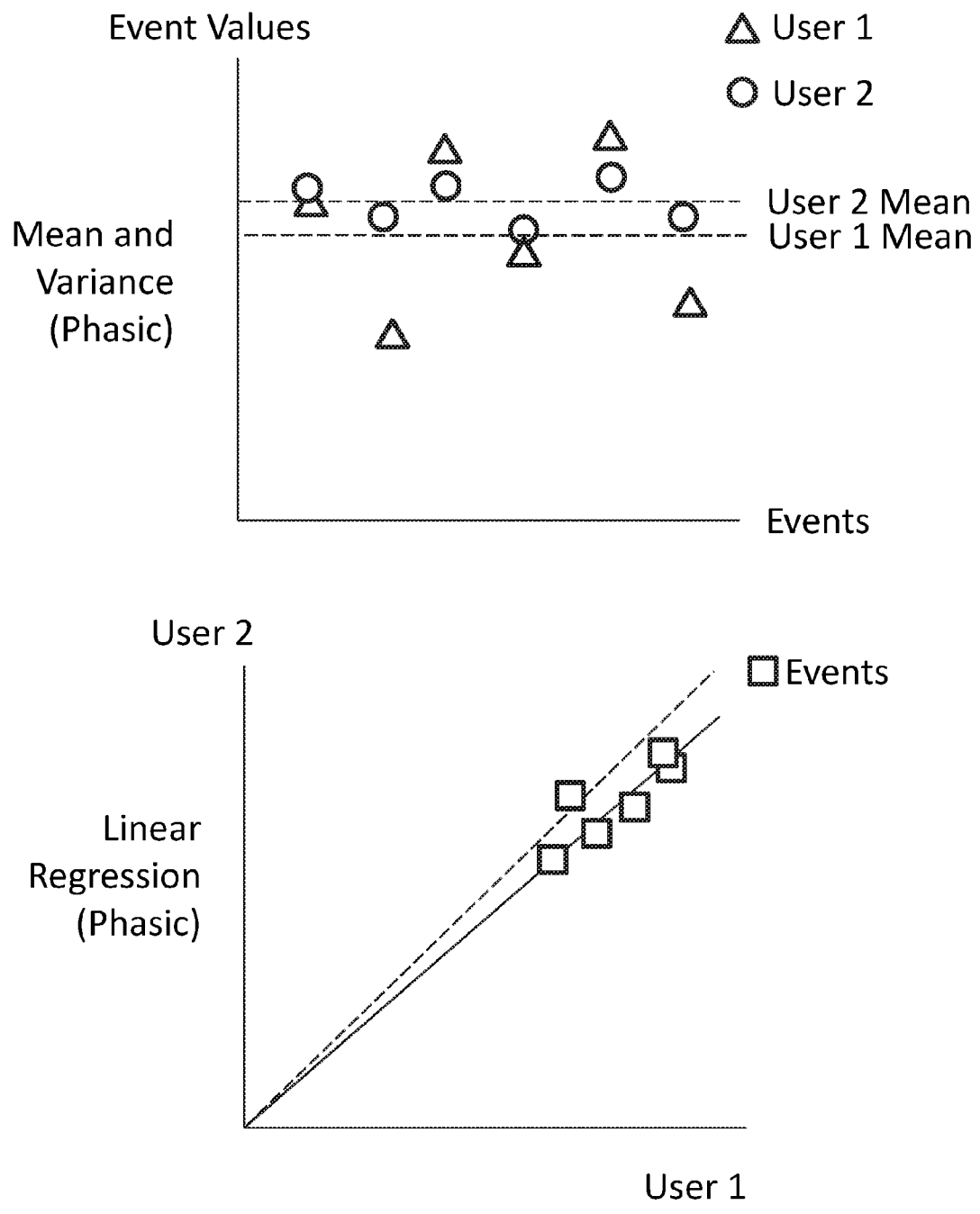
FIG. 7 is a diagram illustrating an example linear regression and an example determination of a variance of phasic data for two users in accordance with certain aspects of the present disclosure.

FIG. 7 is a diagram illustrating an example linear regression and an example determination of a variance of phasic data for two users in accordance with certain aspects of the present disclosure. In some implementations, the processed sensor data (e.g., tonic data, phasic data, and event value) can be statistically analyzed by the compatibility algorithm 130 to provide a quantitative measure of compatibility. One type of statistical analysis that can be applied can include comparing the variance in a particular data type, or set of event values, between two users. In this example, user 1 shows a larger variance in phasic data than user 2. Also, in the example of FIG. 7, user 1 shows a less phasic response as compared to user 2, based on the mean of event values identified in their phasic data.

Also referring to the example of FIG. 7, a comparison can be made between the event values of the phasic events common to both users (shown by squares in the lower plot). In this example, a scatter plot of the phasic events shows that while there is more variation in the phasic data in user 2 than in the phasic data of user 1, the best fit (solid) line through both sets of phasic data, determined by linear regression, are closely matched in slope. If the best-fit line was along the dashed line, this would indicate a perfect linear correlation between user 1 and user 2, in terms of the plotted events. This can suggest that user 1 and user 2, on average, exhibit a good degree of harmony and compatibility. Either or both of the linear regression and variance determination can be used to calculate the compatibility score 120.

The particular examples described herein for the specific analysis of tonic and/or phasic data are not intended to be excluding of other implementations that involve other types of sensor data. For example, variance calculations and linear regression analysis can also be applied to heart rate sensor data, breathing rate sensor data, brain wave sensor data, etc.

In some implementations, compatibility algorithm 130 can generate the compatibility score 120 based on two features of the analyzed sensor data. The first feature can be a comparison of the ratios of the variance in a particular type of data between two users. The second feature can be a comparison of the linear regressions of a particular type of data between two users.

Figure 8:
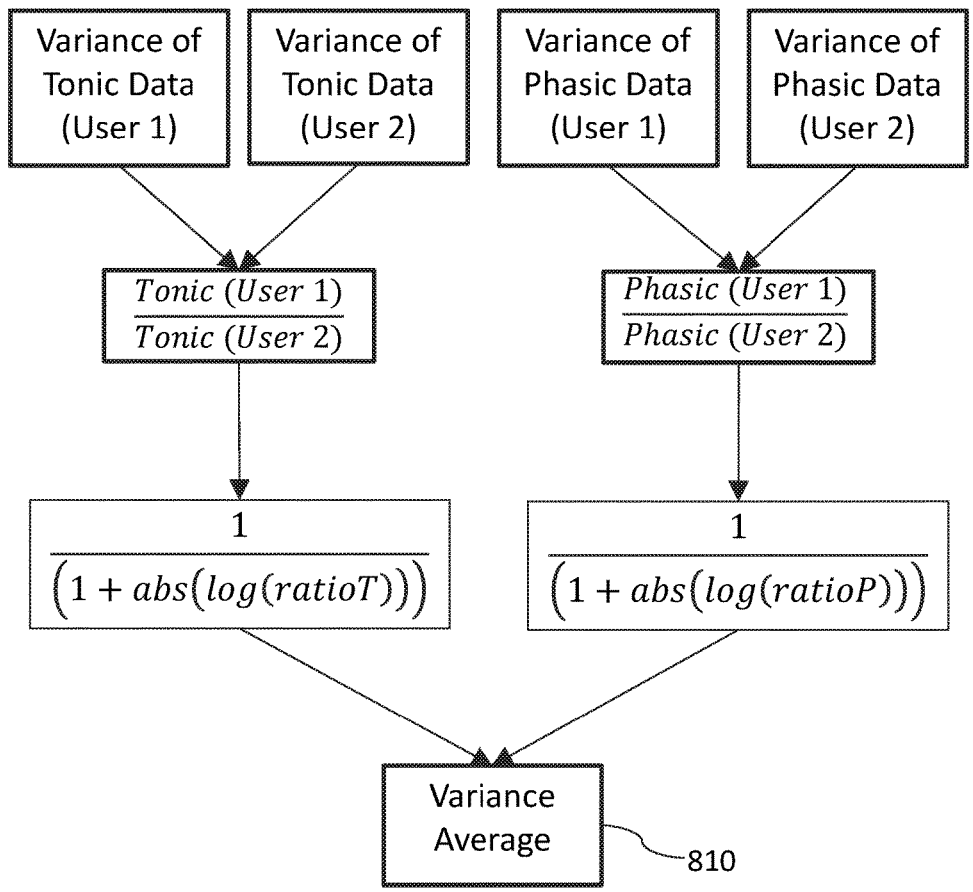
FIG. 8 is a diagram illustrating an example of a process for comparing the variance of sensor data for two users in accordance with certain aspects of the present disclosure.

FIG. 8 is a diagram illustrating an example of a process for comparing the variance of sensor data for two users in accordance with certain aspects of the present disclosure. The variance of a desired subset of data (e.g., tonic data or phasic data) for two users can be expressed as a ratio. This ratio can generally reflect the degree of harmony or compatibility between two users, when considering that particular type of data. For example, two users who are compatible in their tonic data may have a ratio close to one. Two users who are less compatible may have a ratio significantly larger than one or smaller than one. In some implementations, the compatibility algorithm 130 can calculate a first ratio (ratioT in FIG. 8) of a tonic variance between the first user and the second user and a second ratio (ratioP in FIG. 8) of a phasic variance between the first user and the second user. In some implementations, the ratios can then be input to the formula, $$\frac{1}{(1 + \text{abs}(\log(\text{ratio})))}. \tag{1}$$

Eqn. 1 provides a number between 0 and 1. Because there can be more than one metric (e.g., the result of Eqn. 1) for comparison, an average of the available metrics can be calculated. In the example of FIG. 8, the two numbers resulting from Eq. 1 for the tonic and phasic data can be averaged and the resulting "variance average" 810 can reflect a degree of similarity between the variance in the sensor data between the two users. The variance average 810 can be used in the final determination of the compatibility score 120.

Figure 9:
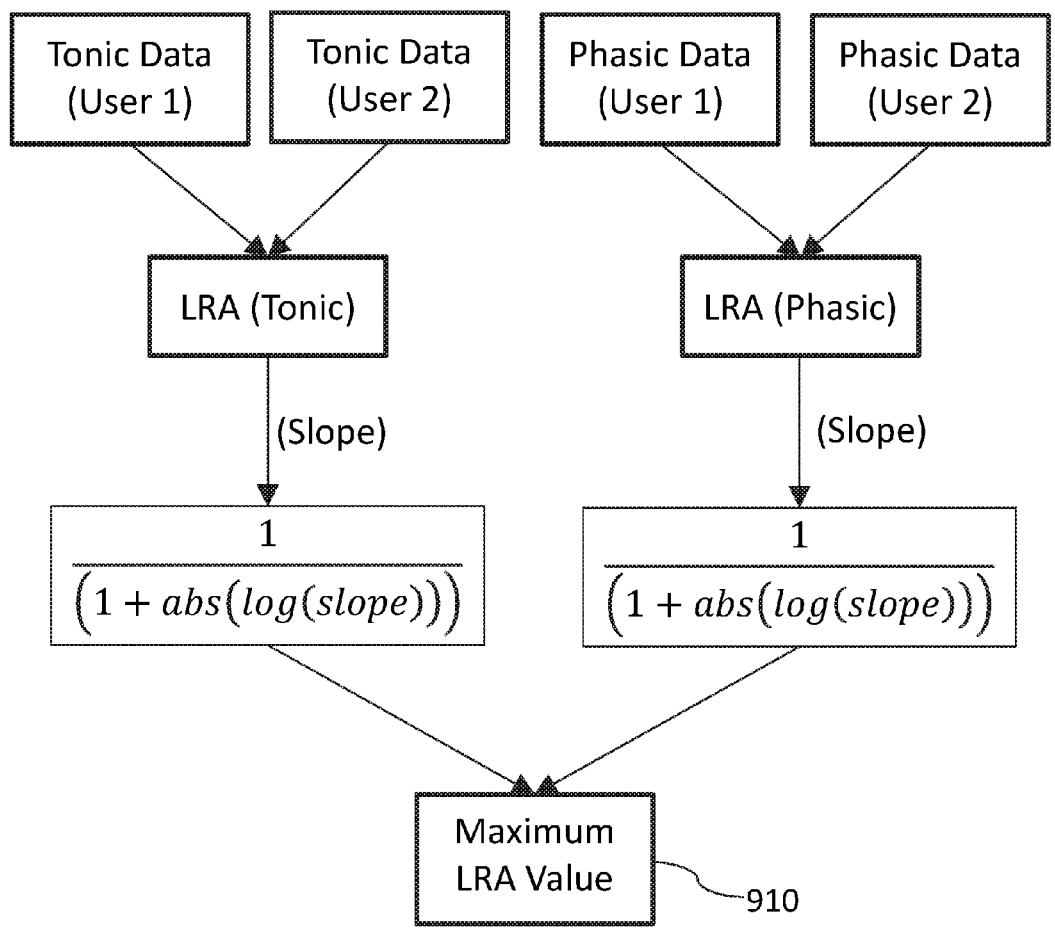
FIG. 9 is a diagram illustrating an example of a process for comparing the linear regression analyses of sensor data for two users in accordance with certain aspects of the present disclosure.

FIG. 9 is a diagram illustrating an example of a process for comparing the linear regression analyses of sensor data for two users in accordance with certain aspects of the present disclosure. In some implementations, generating the compatibility score 120 can include performing a linear regression analysis of the tonic data and the phasic data of the first user and the second user. The linear regression analysis can compare the event values of tonic data of a first user with the event values of the tonic data of a second user to generate a best-fit lines through their respective data sets. Similar to the evaluation of the ratios of the variance, the slopes resulting from the linear regression analysis for the first user and the second user can be evaluated with Eqn. 1. This can generate two numbers between zero and one that can represent the degree of correlation or harmony based on the linear regression analysis of the same types of sensor data (e.g., tonic or phasic). The greater of these two numbers can be stored by the system and is referred to herein as the "maximum LRA value" 910.

Figure 10:
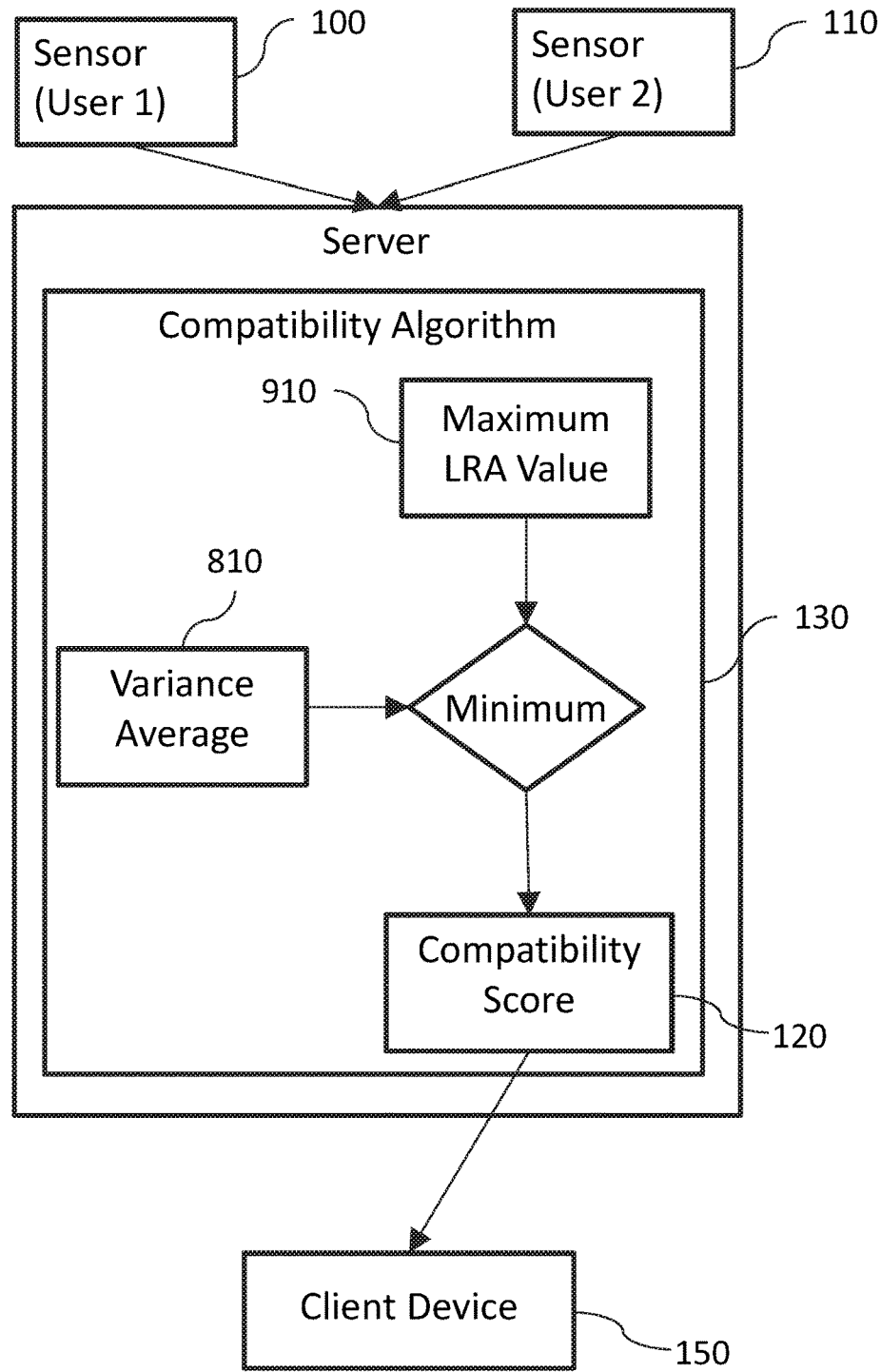
FIG. 10 is a diagram illustrating a system for analyzing the sensor data for two users and providing a compatibility score in accordance with certain aspects of the present disclosure.

FIG. 10 is a diagram illustrating a system for analyzing the sensor data for two users and providing a compatibility score in accordance with certain aspects of the present disclosure.

Once the variance average 810 and the maximum LRA value 910 of the corresponding types of sensor data (e.g., tonic or phasic) are calculated, the minimum of the two can be provided as the compatibility score 120. In this way, the compatibility score 120 can be proportional to an average of the first ratio and the second ratio, and the compatibility score 120 can also be proportional to a measure of agreement in the linear regression analysis for the first user and the second user. The linear regression analysis between the event values of a first user and a second user or group are most in agreement when the line through their event values is along the 45 degree line of their linear regression plot (e.g., the dashed line in FIG. 7). This proximity to the 45 degree line can be one type of measure of agreement of the event values reflected in the linear regression analysis. The further that the linear regression is from this ideal, the lower the LRA value.

Because the system includes a decision point (e.g., determining a minimum) the compatibility score is only proportional to the variance average 810 when the variance average is less than maximum LRA value 910. Conversely, when the maximum LRA value 910 is less than the variance average 810, the compatibility score 120 is proportional to the maximum LRA value 910. By returning the minimum of the compatibility based on the linear regression analysis of the sensor data and the variance of the sensor data, the compatibility algorithm 130 can provide a lower bound quantification of the compatibility or harmony between the two users. In other implementations, the maximum can be used to provide an upper bound quantification of the compatibility between two users.

Other implementations can perform similar operations as the above but, for example, with other expressions instead of Eqn. 1. The above example is not intended to be limiting. In general, the compatibility algorithm 130 can take a collection of sensor data and separate the sensor data into components that can be present in the sensor data (e.g., tonic and phasic) and then analyze the components (or the raw sensor data itself) to determine similarities and differences in the raw or processed sensor data for the two users. The degree of similarity or difference can then be returned by the server 115 as a compatibility score 120 for presentation, storage, or display on a client device 150.

Figure 11:
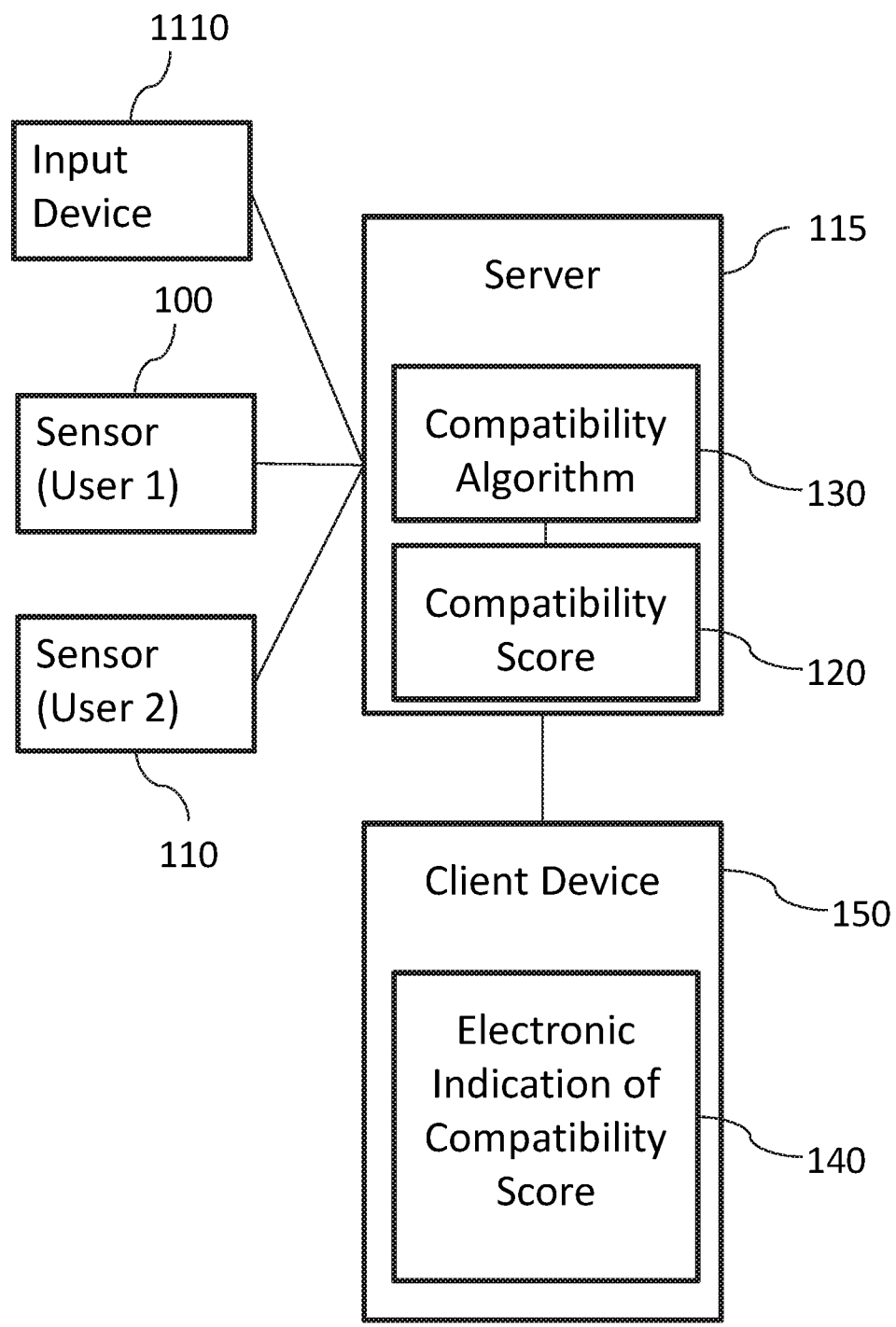
FIG. 11 illustrates a simplified system for generating and presenting a compatibility score based on sensor data and an evaluation of the sensor data received from an input device in accordance with certain aspects of the present disclosure.

FIG. 11 illustrates a simplified system for generating and presenting a compatibility score 120 based on sensor data and an evaluation of the sensor data received from an input device 1110 in accordance with certain aspects of the present disclosure.

In some implementations, users can input, through an input device 1110, information relating to the analysis for themselves or another user. The system can receive an evaluation from the input device 1110 where the user characterizes the first sensor data or the second sensor data in an event window 610. The compatibility score 120 can then be based in part on the evaluation. For example, a user can review the sensor data and at various points in the sensor data (e.g., peaks, valleys, or other features related to an event) can add, through the input device 1110, an evaluation of the event. The evaluation can include, for example, a numerical rating, a verbal description (e.g., "good," "average," or "bad"), a video of the user reacting to an event, or the like. In the case of verbal or video capture of a user's evaluation, voice and/or image recognition software can be used to convert the input from the input device 1110 to an evaluation that can be interpreted by the compatibility algorithm 130. The quantified and/or converted evaluation can be used to, for example, modify event values, adjust tonic or phasic ratios, train a machine learning algorithm (when the compatibility algorithm 130 is based in part on a machine learning algorithm), or the like.

User preferences can be selected and entered by the user at the input device 1110. These user preferences can include specifying a kernel used in the discrete decomposition analysis for defining the shape of the impulses that are reflected in the sensor data. In other implementations, the time window used for clustering can be specified by a user. Also, in other implementations, the user can specify multipliers or weights for specifying the contribution of the mean of the analyzed sensor data or the variance of the analyzed sensor data.

A user can, through an input device 1110 such as a clicker (a device that can be toggled to indicate that an event occurred), a microphone, or a camera, specify a type of event that corresponds to the sensor data (e.g., a date, a greeting, a farewell, etc.). The type of event can be added to the sensor data as an attribute or other form of metadata that associates the type of event with some portion of the sensor data that corresponds to the event. For example, a spike in the sensor data for a heart rate sensor can be associated with a type of event by adding a text attribute such as "pain" to the portion of the sensor data (or the event window 610 as discussed in FIG. 6) that indicates the increased heart rate. Other types of attributes that can be added to the sensor data can include a time, location, intensity, or the like. These attributes can be used to further classify and provide a basis for correlation of the sensor data. For example, the compatibility score 120 can be generated based at least on a comparison of two persons' sensor data that corresponds to a physical activity such as jogging, where the sensor data for the two users have attributes that identify the portions of the sensor data acquired when they were jogging.

In some implementations, users can define which aspects of an event or features of the sensor data will bear more weight in the analysis process. The compatibility algorithm 130 can use data analysis to determine the existence of a desired feature in a potential match. This can include, for example, the system receiving user input from the first user specifying a desired feature of the second user. As a result, the compatibility algorithm 130 can increase the compatibility score 120 when the second sensor data reflects the desired feature.

These desired features can reflect a desired physiological, emotional, or personality trait in a potential match. For example, a first user may want a certain degree of calmness or excitability in a match. In some cases, a calmness can be reflected in or related to the amount of tonic sensor data acquired from a second user as compared to the amount of phasic sensor data. In such implementations, a user can configure the compatibility algorithm 130 to weight the tonic data more heavily than the phasic data when determining compatibility. In another implementation, a user can configure the compatibility algorithm 130 to weight the linear regression analysis more than the variance analysis. These weightings can be entered through a user interface, supplied by a configuration file read by the compatibility algorithm 130, or the like.

Therefore, in some implementations, a first user can select, at a graphical interface of an input device, the desired feature of the second user from a predefined list. The predefined list can include, for example, a calmness and an excitability. In this example, the compatibility score can be based at least on an objective determination that the second user has the desired feature through analysis of the second sensor data. The calmness or the excitability can be determined from the objective determination by the compatibility algorithm 130 based at least on a minimum mean or a maximum variance of the tonic data or the phasic data of the second user.

The systems and methods described herein can include applying one or more machine learning algorithms to, for example, generate a decision or compatibility score 120. In some implementations, the machine learning algorithm can be trained with a predefined training data set. In other implementations, the machine learning algorithm can be trained during use by a user providing user input that evaluates the accuracy of the decision or compatibility score 120. Such an approach has been previously discussed with regard to the inputting of user preferences and a user's evaluation of an event.

In some implementations, the machine learning algorithm can be, for example, one or more of: Ordinary Least Squares Regression (OLSR), Linear Regression, Logistic Regression, Stepwise Regression, Multivariate Adaptive Regression Splines (MARS), Locally Estimated Scatterplot Smoothing (LOESS), k-Nearest Neighbor (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, Least-Angle Regression (LARS), Classification and Regression Tree (CART), Iterative Dichotomiser 3 (ID3), C4.5 and C5.0 (different versions of a powerful approach), Chi-squared Automatic Interaction Detection (CHAID), Decision Stump, M5, Conditional Decision Trees, Naive Bayes, Gaussian Naive Bayes, Multinomial Naive Bayes, Averaged One-Dependence Estimators (AODE), Bayesian Belief Network (BBN), Bayesian Network (BN), k-Means, k-Medians, Expectation Maximisation (EM), Hierarchical Clustering, Apriori algorithm, Eclat algorithm, Perceptron, Back-Propagation, Hopfield Network, Radial Basis Function Network (RBFN), Deep Boltzmann Machine (DBM), Deep Belief Networks (DBN), Convolutional Neural Network (CNN), Stacked Auto-Encoders, Boosting, Bootstrapped Aggregation (Bagging), AdaBoost, Stacked Generalization (blending), Gradient Boosting Machines (GBM), Gradient Boosted Regression Trees (GBRT), and Random Forest.

The above example of a compatibility algorithm 130 providing a compatibility score 120 was provided in terms of a single type of sensor data (e.g., only electro-dermal activity). Other implementations can, in general, be generalized to include an arbitrary number of types of sensor data acquired by an arbitrary number of sensors or sensor devices. For example, instead of only analyzing a single type (e.g., dimension) of the objective data (e.g., sensor data), an additional type of objective data (e.g., blood pressure data) or subjective data (e.g., a desired outcome or evaluation) can be included. In this way, any number or types of data can act as discrete inputs to the compatibility algorithm 130. In implementations where the compatibility algorithm 130 is a neural network or deep belief network, each type of data can be the input to an input node.

To determine an individual's compatibility with a group, or to compare an individual's response to that of a group, the corresponding sensor data of the individuals in the group can be aggregated. For example, if a user's response to a stimulus is different than that of the typical member of a potential group, then the system (in some implementations using a machine-learning algorithm) can predict that the user is not compatible with the group. In this way, by providing a measure of an individual's compatibility with the group, the overall dynamics of the group can be improved by the potential exclusion or discouragement of participation by users that are determined to likely have a lower compatibility with the existing group. By low compatibility, this can describe a user whose compatibility score is below, for example, an average of the group when considering events that the group participates in, or the user having a compatibility score with the group that is below a predetermined threshold.

The aggregated sensor data can be joined in a tabular format or otherwise appended to pre-existing data entries. In other implementations, the aggregated data can be a processed subset of the sensor data. For example, the aggregated data can be an average, sum, difference, or the like of different groups of sensor data. The aggregation can be performed in any order. For example, the raw data can be aggregated and then a single compatibility score 120 generated. In another implementation, the compatibility score 120 between the user and each member of the group can be calculated and then an average compatibility score 120 can be provided based on the individual scores.

Through a user-interface, a user can select a collection of other users as desired groups. Desired groups can include, for example, emotionally desired groups, which the user can select based on attraction, and rationally desired groups, which the user can select based on a rational belief that such members are the correct matches for them. The user can define the measures (or aspects) of the emotionally desired groups based on, for example, physical appearance, hobbies, personality types, etc. Similarly, the user can define the measures of the rationally desired group selection based on such priorities as, for example, security, love, protection, money, morality, religion, politics, etc.

The system can create a matched group for the user based on the user's desired groups and the harmony and correlation analysis of the user's sensor data and sensor data for the desired group.

In some implementations, the system can provide one or more matches between a user and one or more members of a group. A match can include, for example, a best match (e.g., the highest compatibility score 120 with a member of the group) or a group of matches (e.g., the members of the group that have a compatibility score 120 with the user that exceeds a certain threshold). The threshold for matching can be set by the system, entered by the user, or also defined by one or more members of the group. Any combination of metrics for matching or generating a compatibility score 120 can be used. For example, matching or compatibility can be based on raw data, processed sensor data (e.g., including tonic and/or phasic data), aggregated data of any type, or the like. Matching can also be based on a comparison of the compatibility score 120 between a first user and a particular group and the compatibility score 120 between a second user and the particular group. For example, if one user is very compatible with a particular group, but a second user is not compatible with the same group, then the system can avoid matching the first user with the second user. Such cross-user matching can act as a constraint when generating a final compatibility score 120 for a user with the compatibility algorithm 130.

The raw or processed forms of a user's sensor data, or any compatibility scores 120, can be made available to the user by presentation on, for example, a client device 150 (e.g., smartphone, desktop, laptop, or tablet computer), the local device (used to relay the sensor data), the sensor device, or the like. The sensor data can also be presented to other users that have obtained the necessary electronic permissions. Some implementations of the system described herein can include a permission granting system that allows a user to grant and revoke permission for other users to view and or access their raw or processed sensor data. The permission granting system can have multiple levels of access to sensor data or aggregate data of other interested parties.

In some implementations, the system can receive permission settings entered at an input device by the first user. The system can then restrict, based at least on the permission settings, access by the second user to the sensor data or to the analyzed sensor data generated by the compatibility algorithm 130 when generating the compatibility score 120. In other implementations, the permission settings can be timed to expire at a certain date or time, or remain for a specified length of time before reverting back to a prior, or default, setting.

Permission settings can include, for example, restricting the ability of a second user to view, copy, edit, delete, or the like, any or all of the first user's sensor data or compatibility scores or analysis. Conversely, the user can allow progressively increasing levels of access to a second user based on the level of trust or relationship status between the first user and the second user. In some implementations the permission settings can be automatically adjusted based on a current compatibility score 120.

Implementations of the current subject matter can include, but are not limited to, systems and methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description. Other features and advantages of the subject matter described herein will be apparent from the description and drawings. While certain features of the currently disclosed subject matter are described for illustrative purposes in relation to particular implementations, it should be readily understood that such features are not intended to be limiting.

Although a few embodiments have been described in detail above, other modifications are possible. For example, the method steps depicted in FIGS. 3-5 and described herein do not require the particular order shown, or sequential order, to achieve desirable results.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the description, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Multiple inventions may be set forth according to the limitations of the multiple claims issuing from this disclosure, and such claims accordingly define the invention(s), and their equivalents, that are protected thereby.

The invention claimed is:

1. A computer program product comprising a non-transitory, machine-readable medium storing instructions which, when executed by at least one programmable processor, cause the at least one programmable processor to perform operations comprising:
  receiving, at the at least one programmable processor, first sensor data acquired from a first galvanic skin response sensor monitoring a first user;
  receiving, at the at least one programmable processor, second sensor data acquired from a second galvanic skin response sensor monitoring a second user;
  receiving user input from the first user specifying a desired feature of the second user;
  generating, at the at least one programmable processor, a compatibility score between the first user and the second user, the generating comprising:
    executing a compatibility algorithm that performs an ongoing analysis of the first sensor data to generate the compatibility score based at least on a comparison of at least one type of response contained in the first sensor data and the second sensor data, where the monitoring of the first user is performed simultaneous with the ongoing analysis of the first sensor data; and
    increasing, by the compatibility algorithm, the compatibility score when the second sensor data reflects the desired feature; and
  generating, at a client device, an electronic indication of the compatibility score.

2. The computer program product of claim 1, wherein the at least one type of response includes a tonic response and a phasic response, wherein the first sensor data includes first phasic data and first tonic data, and wherein the second sensor data includes second phasic data and second tonic data, the phasic data corresponding to the phasic response and the tonic data corresponding to the tonic response, the operations further comprising:
  separating, by at least a first discrete decomposition analysis, the first sensor data into a first tonic response and a first phasic response; and
  separating, by at least a second discrete decomposition analysis, the second sensor data into a second tonic response and a second phasic response.

3. The computer program product of claim 1, further comprising extracting first tonic data and second tonic data from the first sensor data and the second sensor data, wherein the comparison is further based on the first tonic data and the second tonic data.

4. The computer program product of claim 3, further comprising extracting first phasic data and second phasic data from the first sensor data and the second sensor data, wherein the comparison is further based on the first phasic data and the second phasic data.

5. The computer program product of claim 4, further comprising generating the compatibility score by at least performing statistical analysis of first tonic data and second tonic data extracted from the first sensor data and the second sensor data.

6. The computer program product of claim 1, further comprising generating the compatibility score by at least performing statistical analysis of first phasic data and second phasic data extracted from the first sensor data and the second sensor data.

7. The computer program product of claim 1, further comprising:
  performing a first statistical analysis of first tonic data and second tonic data extracted from the first sensor data and the second sensor data; and
  performing a second statistical analysis of first phasic data and second phasic data extracted from the first sensor data and the second sensor data, wherein the compatibility score is based at least on the first statistical analysis and the second statistical analysis.

8. The computer program product of claim 7, the generating of the compatibility score further comprising:
  performing a first linear regression analysis of the tonic data of the first user and the second user; and
  calculating a first ratio of a tonic variance between the first user and the second user.

9. The computer program product of claim 8, the generating of the compatibility score further comprising:
  performing a second linear regression analysis of the phasic data of the first user and the second user; and
  calculating a second ratio of a phasic variance between the first user and the second user.

10. The computer program product of claim 9, wherein the compatibility score is proportional to an average of the first ratio and the second ratio, and the compatibility score is proportional to a measure of agreement in the first linear regression analysis or the second linear regression analysis for the first user and the second user.

11. The computer program product of claim 10, wherein at least one of the first sensor data or the second sensor data includes an event window containing a number of peaks in the first sensor data or the second sensor data.

12. The computer program product of claim 11, further comprising clustering the number of peaks in the first sensor data or the second sensor data to generate an event value for a portion of the first sensor data or the second sensor data, the clustering comprising:
   filtering the first sensor data or the second sensor data to identify the number of peaks in the first sensor data or the second sensor data present in the event window that have an amplitude of at least a threshold value; and
   generating the event value based on the number of the peaks in the event window, wherein the first ratio, the second ratio, or the linear regression analysis is based at least on the event value.

13. The computer program product of claim 1, further comprising:
   receiving, from an input device, an evaluation characterizing the first sensor data or the second sensor data in an event window, wherein the compatibility score is based in part on the evaluation.

14. The computer program product of claim 1, further comprising:
   selecting, by a first user at a graphical interface of an input device, the desired feature of the second user from a predefined list that includes a calmness or an excitability, wherein the compatibility algorithm generates the compatibility score based at least on an objective determination that the second user has the desired feature through analysis of the second sensor data.

15. The computer program product of claim 14, wherein the calmness or the excitability are determined based at least on statistical analysis of the tonic data or the phasic data of the second user.

16. The computer program product of claim 1, further comprising:
   receiving permission settings entered at an input device by the first user; and
   restricting, based at least on the permission settings, access by the second user to at least one of first sensor data or analyzed first sensor data generated by the compatibility algorithm when generating the compatibility score.

17. The computer program product of claim 1, further comprising:
   filtering, by at least applying principle component analysis, the sensor data to exclude one or more types of the sensor data, the filtering removing at least one component of the sensor data as identified by the principle component analysis.

18. A system comprising:
   a first galvanic skin response sensor configured to monitor a first user;
   a second galvanic skin response sensor configured to monitor a second user;
   at least one programmable processor; and
   a non-transient machine-readable medium storing instructions which, when executed by the at least one programmable processor, cause the at least one programmable processor to perform operations comprising:
      receiving, at the at least one programmable processor, first sensor data acquired from the first galvanic skin response sensor monitoring the first user;
      receiving, at the at least one programmable processor, second sensor data acquired from the second galvanic skin response sensor monitoring the second user;
      receiving user input from the first user specifying a desired feature of the second user;
      generating, at the at least one programmable processor, a compatibility score between the first user and the second user, the generating comprising:
         executing a compatibility algorithm that performs an ongoing analysis of the first sensor data to generate the compatibility score based at least on a comparison of at least one type of response contained in the first sensor data and the second sensor data, where the monitoring of the first user is performed simultaneous with the ongoing analysis of the first sensor data; and
         increasing, by the compatibility algorithm, the compatibility score when the second sensor data reflects the desired feature; and
      generating, at a client device, an electronic indication of the compatibility score.

19. The system of claim 18, further comprising a complementary device configured to receive user input and add an evaluation to the first sensor data or the second sensor data, the evaluation providing a numerical weight to the first sensor data or the second sensor data when generating the compatibility score.

* * * * *